United States Patent
Kundu et al.

(10) Patent No.: US 10,549,602 B2
(45) Date of Patent: Feb. 4, 2020

(54) SYSTEM, METHOD AND COMPUTER PROGRAM PRODUCT FOR AN AIR QUALITY AMELIORATION ACTION

(71) Applicant: International Business Machines Corporation, Armonk, NY (US)

(72) Inventors: Ashish Kundu, Elmsford, NY (US); Clifford A. Pickover, Yorktown Heights, NY (US); Maja Vukovic, New York, NY (US); Komminist Weldemariam, Nairobi (KE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 229 days.

(21) Appl. No.: 15/396,931

(22) Filed: Jan. 3, 2017

(65) Prior Publication Data

US 2018/0186212 A1   Jul. 5, 2018

(51) Int. Cl.

| | | |
|---|---|---|
| *A61L 9/00* | (2006.01) | |
| *B60H 3/00* | (2006.01) | |
| *B01D 53/02* | (2006.01) | |
| *B60H 1/00* | (2006.01) | |
| *A61L 9/20* | (2006.01) | |
| *A61L 9/16* | (2006.01) | |
| *B60H 3/06* | (2006.01) | |
| *B01D 46/44* | (2006.01) | |
| *B01D 46/46* | (2006.01) | |

(52) U.S. Cl.
CPC ............... *B60H 1/008* (2013.01); *A61L 9/16* (2013.01); *A61L 9/20* (2013.01); *B60H 1/00821* (2013.01); *B60H 1/00971* (2013.01); *B60H 3/06* (2013.01); *A61L 2209/111* (2013.01); *A61L 2209/14* (2013.01); *A61L 2209/22* (2013.01); *B01D 46/442* (2013.01); *B01D 46/46* (2013.01); *B60H 2003/0683* (2013.01)

(58) Field of Classification Search
CPC ...... A61L 9/22; B60W 50/0098; B60H 1/008; B60H 1/00821; F24F 11/0001
USPC ..... 422/3–5, 22, 28, 83, 105, 119–120, 186, 422/305–306; 96/108, 222–223; 55/522; 95/90, 273; 454/156
See application file for complete search history.

(56) References Cited

U.S. PATENT DOCUMENTS

| | | | |
|---|---|---|---|
| 2008/0161986 A1 | 7/2008 | Breed | |
| 2014/0309893 A1 | 10/2014 | Ricci | |
| 2015/0168556 A1 | 6/2015 | Zhu et al. | |
| 2015/0233719 A1* | 8/2015 | Cudak | B60R 25/01 701/23 |

(Continued)

OTHER PUBLICATIONS

Mel, et al. "The NIST Definition of Cloud Computing". Recommendations of the National Institute of Standards and Technology. Nov. 16, 2015.

*Primary Examiner* — Monzer R Chorbaji
(74) *Attorney, Agent, or Firm* — Eyal Gilboa, Esq.; McGinn IP Law Group, PLLC (57) ABSTRACT

A computer-implemented air quality amelioration method, computer program product, and system for a self-driving vehicle, the method including detecting a value of an air quality within a cabin of the self-driving vehicle and performing an amelioration action to improve the value of the air quality based on the detection of the value of the air quality being less than a predetermined value.

19 Claims, 4 Drawing Sheets

(56) References Cited

U.S. PATENT DOCUMENTS

2015/0360544 A1\* 12/2015 Fruehsorger ............. B60H 3/06
                   96/19

\* cited by examiner

SYSTEM, METHOD AND COMPUTER PROGRAM PRODUCT FOR AN AIR QUALITY AMELIORATION ACTION

BACKGROUND

The present invention relates generally to an air quality amelioration method, and more particularly, but not by way of limitation, to a system, method, and computer program product for performing an air quality amelioration action in a cabin of a vehicle based on a detection of poor air quality.

Often, the air quality in vehicles may be poor or may decrease for many reasons which relate to both passenger safety or aesthetics (e.g., if odors are present). In a self-driving car (SDC) or self-driving vehicle (SDV), much of the car is automated (i.e., not under user control), and it would be advantageous to provide a passenger with an automated system for improving air quality as useful.

SUMMARY

In an exemplary embodiment, the present invention can provide a computer-implemented air quality amelioration method for a self-driving vehicle, the method including detecting a value of an air quality within a cabin of the self-driving vehicle and performing an amelioration action to improve the value of the air quality based on the detection of the value of the air quality being less than a predetermined value.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

The invention will now be described with reference to FIG. 1-4, in which like reference numerals refer to like parts throughout. It is emphasized that, according to common practice, the various features of the drawings are not necessarily to scale. On the contrary, the dimensions of the various features can be arbitrarily expanded or reduced for clarity.

Figure 1:
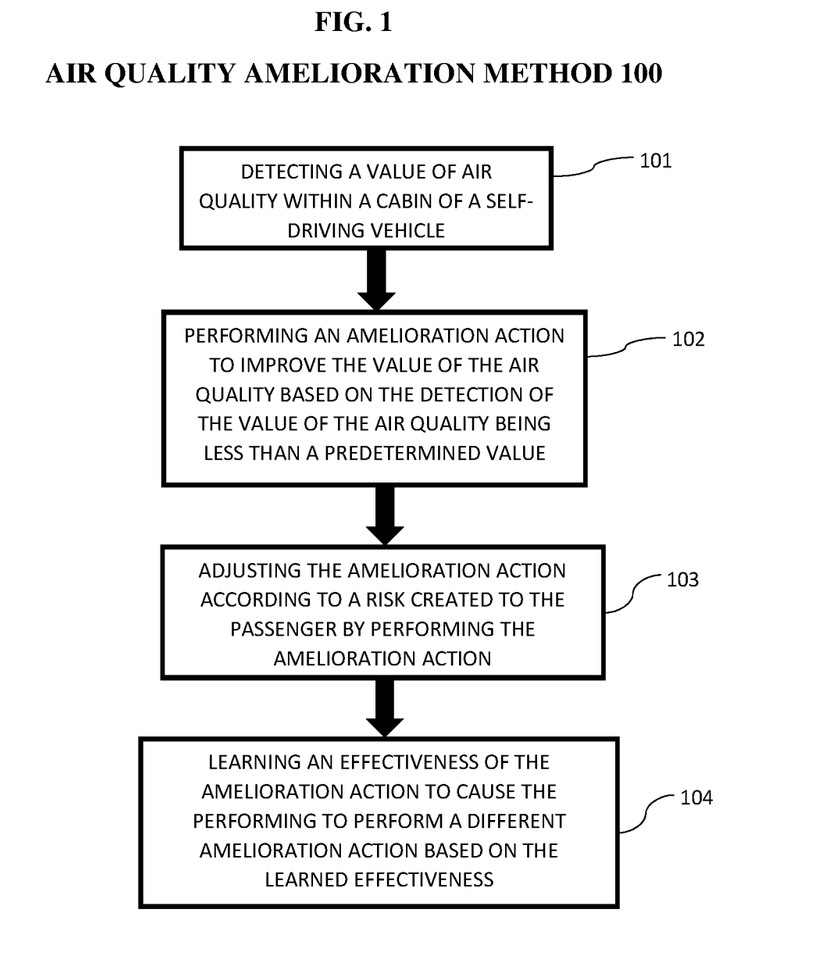
FIG. 1 exemplarily shows a high-level flow chart for an air quality amelioration method 100.

With reference now to the example depicted in FIG. 1, the air quality amelioration method 100 includes various steps to detect an air quality (i.e., a value representing the air quality) within a vehicle and perform an amelioration action to improve the value of the air quality. As shown in at least FIG. 2, one or more computers of a computer system 12 according to an embodiment of the present invention can include a memory 28 having instructions stored in a storage system to perform the steps of FIG. 1.

Thus, the air quality amelioration method 100 according to an embodiment of the present invention may act in a more sophisticated, useful and cognitive manner, giving the impression of cognitive mental abilities and processes related to knowledge, attention, memory, judgment and evaluation, reasoning, and advanced computation. A system can be said to be "cognitive" if it possesses macro-scale properties—perception, goal-oriented behavior, learning/memory and action—that characterize systems (i.e., humans) generally recognized as cognitive.

Although one or more embodiments (see e.g., FIGS. 2-4) may be implemented in a cloud environment 50 (see e.g., FIG. 3), it is nonetheless understood that the present invention can be implemented outside of the cloud environment.

In step 101, a value of an air quality within a cabin of a self-driving vehicle is detected. It is noted that although the embodiments will be described referencing a self-driving vehicle, the invention is not limited thereto. That is, the method 100, system, and computer program product can be realized in a conventional user driven vehicle to, for example, reduce the risk of accidents caused by distraction with the user manually performing an amelioration action (e.g., making the vehicle more "hands free").

For example, in step 101, a value of air quality (e.g., a value indicating poor (or good) air quality) can be detected by using sensors to detect odors, deleterious chemicals, carbon monoxide or dioxide, low level of oxygen, tobacco smoke, airborne particulate matter, etc. Passengers may also provide feedback regarding their perception of air quality. In other words, the cabin of the vehicle is monitored in step 101 to detect if the air quality is poor (i.e., below a predetermined threshold as measured by the sensors, with optionally the passenger feedback).

In some embodiments, the detection may consider exposure to bacterial endotoxin and fungal $\beta$-(1,3)-glucan in determining the value of air quality, which may also occur in the car indoor environment and can induce major respiratory symptoms. In other embodiments, a consideration may be made regarding polybrominated diphenyl ethers (PBDEs), hexabromocyclododecanes (HBCDs), and tetrabromobiphenol-A (TBBP-A), flame retardants, aromatic and aliphatic hydrocarbons, microorganisms, mold spores, (or an estimation regarding such presence), etc. It is noted that, even if some sensors and tests are difficult to employ, an "estimation" may be made of certain contaminants based on the known presence of animals, food, dirt, etc. In other embodiments, the value of the air quality can be based on an exposure to aromatic and aliphatic hydrocarbons.

In other embodiments, the detecting can detect a value of the air quality by consideration of so-called "new car" chemicals based on a risk assessment and temperature (e.g., the danger may persist even when car is not new, and can increase when excessive heat builds up in locked/closed cars during the summer months, causing the levels to rise again due to the heat activation). The chemical mixture may include of volatile organic compounds (VOCs), including formaldehyde; polybrominated diphenyl ethers (PBDEs), used as flame retardants; and phthalic acid esters (phthalates), which are emitted from materials and finishes used to make car interiors, such as plastics, wood, leather, textiles, seat cushions, glues and sealants. Exposure can exacerbate allergy and asthma symptoms and cause eye, nose and throat irritation, cough, headache, general flu-like illnesses, and skin irritation. Some also are known to cause cancer and neurological effects. Alternatively, volatile organic compounds may be detected, coming from cleaning products and processes used in cars.

The detecting can use an anion generator, ozonizer, etc. That is, a monitor for the detection may include a formaldehyde monitoring sensor, a total suspended particulate monitoring sensor, a sulfur dioxide monitoring sensor and a relative humidity monitoring sensor. These sensors may be connected with an air conditioning control microprocessor (or to other components of our amelioration system). The method may further make use of an air standard comparison module, an air conditioning control microprocessor and an air quality feedback module. The vehicle may display an indication of the value of the air quality.

In step 102, an amelioration action is performed to improve the value of the air quality based on the detection of the value of the air quality being less than a predetermined value. The amelioration action may include, for example, opening a vent, turning on a fan, opening a window, sending an emergency message, providing instructions to passengers, deploying of a special air filter, deployment of a special air filter mask worn by the passenger(s), starting the air conditioner, deploying scents to mask the aroma of fowl (or other animals, organic or inorganic substances, etc.) riding with passengers in a self-driving truck, deployment of UV (ultraviolet sterilization, e.g. before a passenger enters the car), the deployment of an air-conditioning filter to absorb some of the volatile organic compounds, etc. In some embodiments, the amelioration action may include an electrostatic field of sufficient strength which may serve as an additional tool to clean the cabin air from sub-micron size particles.

The type of amelioration action to be performed may be decided based on a presence of animals, packages, pets, fowl, and other items in the self-driving car or truck.

In other embodiments, the amelioration action can include re-routing the self-driving vehicle in order to optimize the air quality towards an improved scenario. For example, the self-driving vehicle may take another route in order to ensure better indoor air quality (e.g., avoiding a route near a chemical or insecticide plant, a city dump, a sewage facility, etc.). It applies optimization function to determine the route that has less pollution or better weather (or windows can be opened) in order to improve the air quality in the car than in other routes.

In other embodiments, the amelioration action may include dynamic air purification and disinfection. Indoor dust in the indoor air may be washed out by a water bubbler unit to which disinfection liquid may be added.

In some embodiments, a length of time of exposure of a vehicle passenger may be considered when performing the amelioration action. For example, if the passengers are only in the vehicle for a short trip, the predetermined value may be adjusted lower such that the amelioration action will not be performed during short trips to avoid excess actions by the method.

In step 103, the amelioration action is adjusted according to a risk created to the passenger by performing the amelioration action. That is, some amelioration actions may create a risk to the passengers such as opening a window during a rainstorm. The amelioration action can be adjusted before the amelioration action is performed such that a different amelioration action is performed to avoid the risk. The risk factored into adjusting the amelioration action may include, for example, vehicle speed, a detection of rain, snow, dust, and pollution (which may control the degree to which a window may open), a detection of insects and animals near the car, etc.

It is noted that "risk" and concerns may be elevated when the car detects little children or pets are in the car, because the child or disabled person may not be able to make judgments and perform acts that adults are able to perform and thus need special care. In other words, the risk can include a profile of the passenger to adjust the amelioration action. Also, if a pet is in the car, the risk may change including an increase in the level of distraction of passengers, the possibility that a pet could jump out a window, etc.

A passenger cohort may be considered as part of the risk considered in adjusting the amelioration action. For example, a cohort of users with asthma, allergies, chronic obstructive pulmonary disease (COPD), etc. In some embodiments, a profile of a user is created (e.g., such as a smart phone having a profile of the user syncing with the vehicle) such that the amelioration action is adjusted based on preferences of the user.

In some embodiments, the risk may also include an estimate of road conditions such as tunnels or crowded freeways with a high proportion of diesel trucks (i.e., which do not allow window opening to be a safe method to decrease UFP (ultrafine particles) levels significantly).

The risk factor considered to adjust the amelioration action may also utilize IBM's Green Horizon Framework™ to determine a type of amelioration action. The invention may extend such framework by utilizing sensors to detects bad smell(s) from outside, such as in case the SDC is passing by garbage collection or dumping area, a sensor detect a garbage truck is passing by, etc.

In step 104, an effectiveness of the amelioration action is learned to cause the performing to perform a different amelioration action based on the learned effectiveness. That is, the learning can be based on odor and smell sensory data analysis to detect bad shoe, body, etc. smell(s) and regulate the interior condition based on such analysis. In other embodiments, if the previous amelioration action includes opening a window to increase the air quality and the previous action was not effective as determined by the learning, the next amelioration action for a similar value of air quality is different because the last action was not effective to increase the air quality. In other words, if the effectiveness is less than a second predetermined value, the amelioration action is determined not to "be effective" and a different amelioration action will be performed a next time that the value of the air quality is less than the predetermined value.

For example, a different amelioration action is "learned" over time by taking actions and sensing results and/or receiving user feedback. A highly-localized weather forecast is another input to the learning, as it provides access to the air quality levels, and can help predict patterns of, for example, pollen distribution in the air. The method may preserve air based on the anticipated road and weather conditions (e.g. stuck in a long line of vehicles trying to escape from the city due to a potential biochemical hazard, etc.), and will manage the car's air flow correspondingly.

In some embodiments, the risk assessment to adjust the amelioration action may be based on crowdsourcing or community-based risk assessment that further benefits from IoT (Internet of Things)-technology.

In some embodiments, the risk assessment and learning of the effectiveness of actions may consider proximity of mines (e.g., coal mines, natural gas sources, etc.), current external conditions (e.g. driving through a radioactive zone). Moreover, water treatment plants, which may look benign, often create an unpleasant odor for passers in the area.

In some embodiments, an alarm may be triggered if the value of the air quality is less than the predetermined value.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 2:
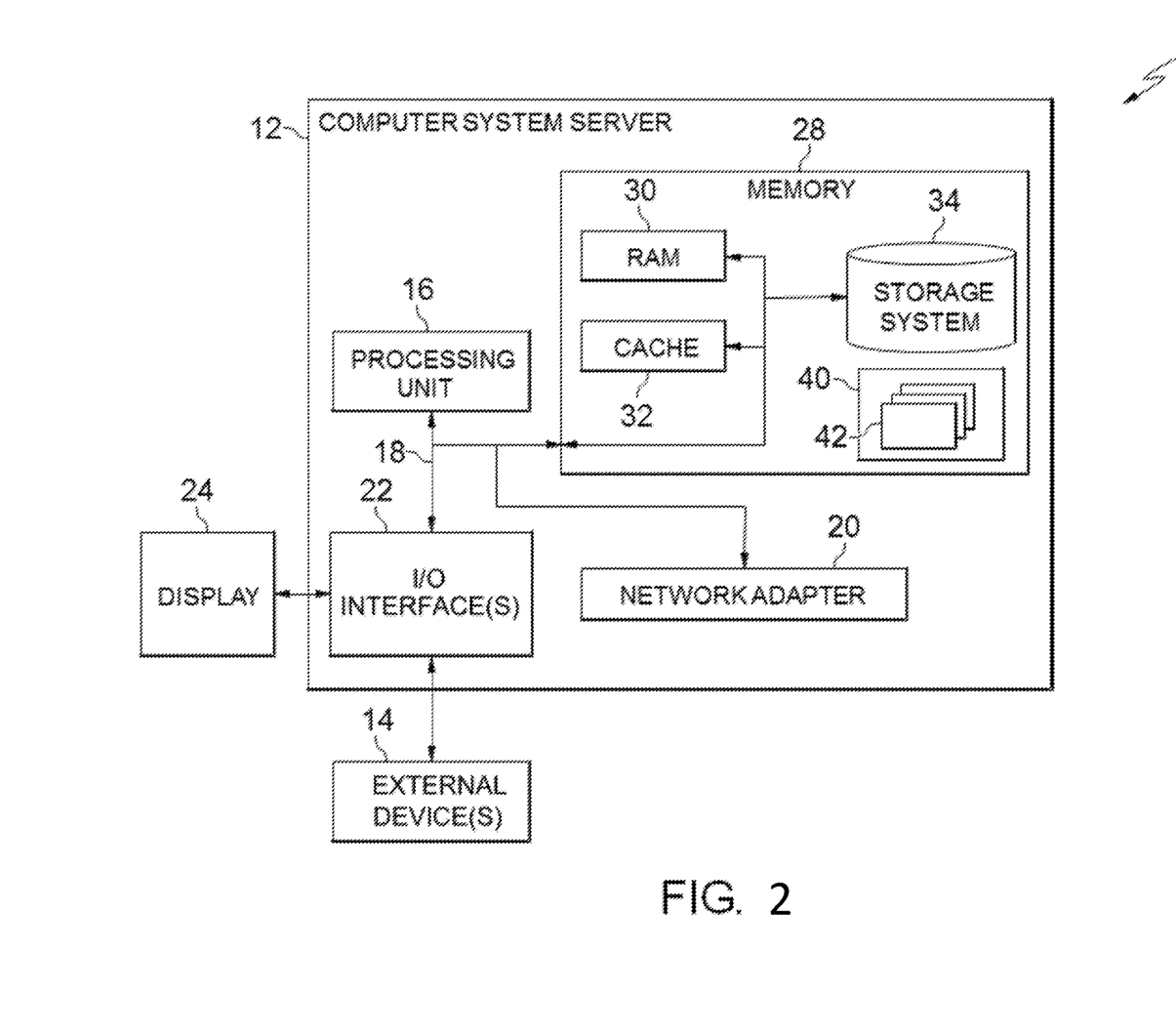
FIG. 2 depicts a cloud computing node 10 according to an embodiment of the present invention.

Referring now to FIG. 2, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 2, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 3:
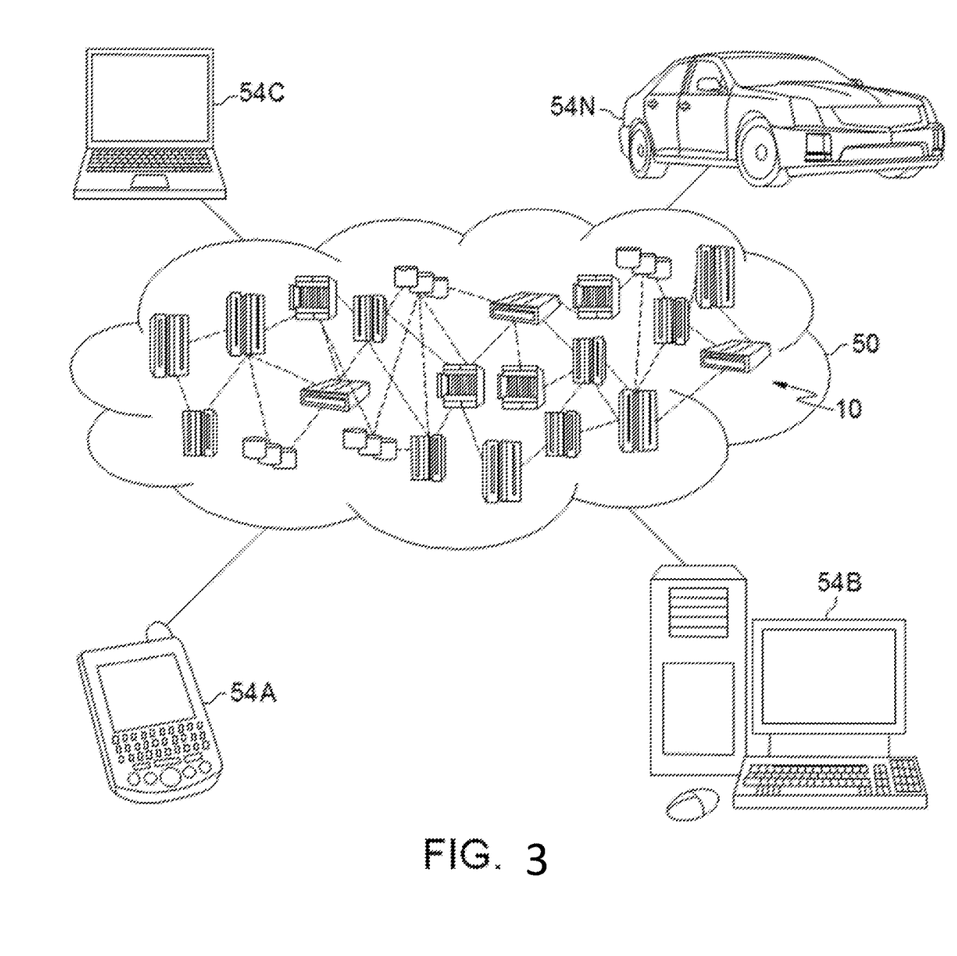
FIG. 3 depicts a cloud computing environment 50 according to an embodiment of the present invention.

Referring now to FIG. 3, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 3 are intended to be illustrative only and that computing nodes 10 and cloud computing environment 50 can communicate with any type of computerized circuit over any type of network and/or network addressable connection (e.g., using a web browser).

Figure 4:
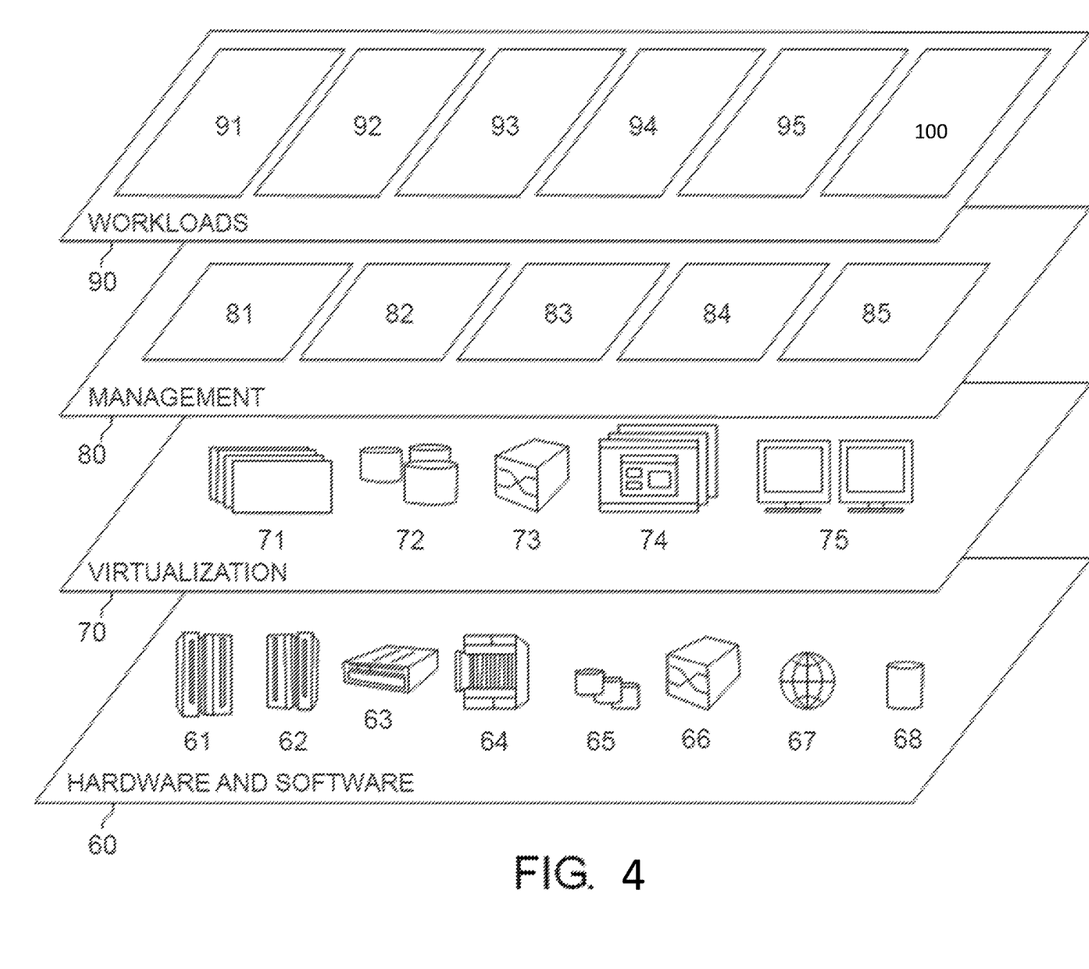
FIG. 4 depicts abstraction model layers according to an embodiment of the present invention.

Referring now to FIG. 4, an exemplary set of functional abstraction layers provided by cloud computing environment 50 (FIG. 3) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the air quality amelioration method 100.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented air quality amelioration method for a self-driving vehicle, the method comprising:
   detecting a value of an air quality within a cabin of the self-driving vehicle;
   requesting a second value of the air quality within the cabin of the self-driving vehicle from a passenger of the self-driving vehicle; and
   performing an amelioration action to improve the value of the air quality based on the detection of the value and the second value of the air quality being less than a predetermined value,
   wherein the detecting detects the value of the air quality by factoring in a length of time that a passenger is exposed to an item causing the value of the air quality.

2. The computer-implemented method of claim 1, further comprising adjusting the amelioration action according to a risk created to a passenger by performing the amelioration action.

3. The computer-implemented method of claim 2, further comprising learning an effectiveness of the amelioration action performed to cause the performing to perform a different amelioration action a next time that the value of the air quality is less than the predetermined value if the effectiveness of the amelioration action is less than a second predetermined value.

4. The computer-implemented method of claim 2, wherein the risk comprises at least one of:
   a speed of the self-driving vehicle;
   a detection of one of rain, snow, dust, and pollution;
   a detection of an insect near the self-driving vehicle;
   a detection of an animal near the self-driving vehicle; and
   a profile of a passenger in the cabin of the self-driving vehicle.

5. The computer-implemented method of claim 2, wherein the risk includes a profile of a cohort of passengers.

6. The computer-implemented method of claim 2, wherein the risk includes an estimate of a road condition that decreases the value of the air quality when the amelioration action is performed.

7. The computer-implemented method of claim 1, further comprising learning an effectiveness of the amelioration action performed to cause the performing to perform a different amelioration action a next time that the value of the air quality is less than the predetermined value if the effectiveness of the amelioration action is less than a second predetermined value.

8. The computer-implemented method of claim 1, wherein the detecting of the value of the air quality uses a sensor for detecting at least one of:
   odors;
   a deleterious chemical;
   carbon monoxide or dioxide;
   an oxygen level;
   a level of non-tobacco smoke;
   a level of tobacco smoke; and
   a airborne particulate matter.

9. The computer-implemented method of claim 1, wherein the amelioration action includes at least one of:
   opening a vent;
   turning on a fan;
   opening a window;
   sending an emergency message;
   providing an instruction to a passenger;
   deploying an air filter;
   starting an air conditioner device;
   deploying a scent to mask an aroma of a smell;
   deploying ultraviolet sterilization; and
   deploying of an air-conditioning filter to absorb a volatile organic compound.

10. The computer-implemented method of claim 1, wherein the value of the air quality is based on an exposure of a passenger to bacterial endotoxin and fungal $\beta$-(1,3)-glucan.

11. The computer-implemented method of claim 1, wherein the value of the air quality is based on an exposure of a passenger to one of polybrominated diphenyl ethers (PBDEs), hexabromocyclododecanes (HBCDs), tetrabromobiphenol-A (TBBP-A), and a flame retardant.

12. The computer-implemented method of claim 1, wherein the value of the air quality is based on an exposure of a passenger to aromatic and aliphatic hydrocarbons.

13. The computer-implemented method of claim 1, wherein the value of the air quality is based on an exposure of the passenger to chemicals in the self-driving vehicle and an effect of a temperature of the self-driving vehicle to the chemicals.

14. The computer-implemented method of claim 1, wherein the amelioration action includes changing a route of the self-driving vehicle to avoid an external event that causes the value of the air quality to decrease.

15. The computer-implemented method of claim 1, embodied in a cloud-computing environment.

16. An air quality amelioration system for a self-driving vehicle, said system comprising:
   a processor; and a memory, the memory storing instructions to cause the processor to perform:

detecting a value of an air quality within a cabin of the self-driving vehicle; and requesting a second value of the air quality within the cabin of the self-driving vehicle from a passenger of the self-driving vehicle; and performing an amelioration action to improve the value of the air quality based on the detection of the value and the second value of the air quality being less than a predetermined value, wherein the detecting detects the value of the air quality by factoring in a length of time that a passenger is exposed to an item causing the value of the air quality.

17. A non-transitory computer-readable recording medium recording an air quality amelioration program for a self-driving vehicle the program causing a computer to perform:

detecting a value of an air quality within a cabin of the self-driving vehicle; and requesting a second value of the air quality within the cabin of the self-driving vehicle from a passenger of the self-driving vehicle; and performing an amelioration action to improve the value of the air quality based on the detection of the value and the second value of the air quality being less than a predetermined value, wherein the detecting detects the value of the air quality by factoring in a length of time that a passenger is exposed to an item causing the value of the air quality.

18. The computer program product of claim 17, further comprising adjusting the amelioration action according to a risk created to a passenger by performing the amelioration action.

19. The computer program product of claim 17, further comprising learning an effectiveness of the amelioration action performed to cause the performing to perform a different amelioration action a next time that the value of the air quality is less than the predetermined value if the effectiveness of the amelioration action is less than a second predetermined value.

* * * * *